US006510343B2

(12) United States Patent
Armstrong et al.

(10) Patent No.: US 6,510,343 B2
(45) Date of Patent: Jan. 21, 2003

(54) METHODS AND APPARATUS FOR TACHYCARDIA RATE HYSTERESIS FOR DUAL-CHAMBER CARDIAC STIMULATORS

(75) Inventors: Randolph Kerry Armstrong, Missouri City, TX (US); Douglas Jason Cook, Minnetonka, MN (US)

(73) Assignee: Intermedics, Inc., Angleton, TX (US)

( * ) Notice: Subject to any disclaimer, the term of this patent is extended or adjusted under 35 U.S.C. 154(b) by 0 days.

(21) Appl. No.: 09/811,931

(22) Filed: Mar. 19, 2001

(65) Prior Publication Data

US 2001/0014817 A1 Aug. 16, 2001

Related U.S. Application Data

(62) Division of application No. 09/332,781, filed on Jun. 14, 1999, now Pat. No. 6,233,485.

(51) Int. Cl.[7] .................................... A61N 1/365
(52) U.S. Cl. .................................... 607/25
(58) Field of Search .................... 607/4, 9, 25, 14

(56) References Cited

U.S. PATENT DOCUMENTS

| | | | | |
|---|---|---|---|---|
| 4,390,022 | A | 6/1983 | Calfee et al. | 128/419 |
| 4,404,972 | A | 9/1983 | Gordon et al. | 128/419 PG |
| 4,452,248 | A | 6/1984 | Keller, Jr. | 128/419 |
| 4,539,992 | A | 9/1985 | Calfee et al. | 128/419 |
| 4,830,006 | A | 5/1989 | Haluska et al. | 607/4 |
| 4,926,863 | A | 5/1990 | Alt | 128/419 PG |
| 5,002,052 | A | 3/1991 | Haluska | 128/419 PG |
| 5,027,815 | A | 7/1991 | Funke et al. | 128/419 PG |
| 5,354,315 | A | 10/1994 | Armstrong et al. | 607/4 |
| 5,514,164 | A | 5/1996 | Mann et al. | 607/25 |
| 5,549,653 | A | 8/1996 | Stotts et al. | 607/4 |
| 5,607,459 | A | 3/1997 | Paul et al. | 607/29 |
| 5,609,615 | A | 3/1997 | Sanders et al. | 607/36 |
| 5,628,776 | A | 5/1997 | Paul et al. | 607/119 |
| 5,630,838 | A | 5/1997 | Prutchi et al. | 607/116 |
| 5,643,328 | A | 7/1997 | Cooke et al. | 607/36 |
| 5,709,712 | A | 1/1998 | Paul et al. | 607/27 |
| 5,713,932 | A | 2/1998 | Gillberg et al. | 607/27 |
| 5,814,088 | A | 9/1998 | Paul et al. | 607/28 |
| 5,873,897 | A | 2/1999 | Armstrong et al. | 607/14 |
| 5,963,418 | A | 10/1999 | Greenwood, Jr. et al. | 361/508 |

FOREIGN PATENT DOCUMENTS

| | | | |
|---|---|---|---|
| EP | 0241102 | 11/1983 | A61N/1/368 |
| EP | 04019A62 | 4/1990 | A61N/1/368 |

*Primary Examiner*—Jeffrey R. Jastrzab
(74) *Attorney, Agent, or Firm*—Schwegman, Lundberg, Woessner & Kluth, P.A.

(57) ABSTRACT

It has been determined that certain dual-chambered cardiac stimulators may operate in a region in which an atrial pacing event may obscure the detection of a ventricular tachyarrhythmia Various exemplary techniques may be used to improve the ability of dual-chamber cardiac stimulators to detect such ventricular events. In accordance with one technique, it is determined whether a ventricular event should be classified as a ventricular tachyarrhythmia. If not, the VA interval is restarted as usual. However, if the ventricular event may be classified as a ventricular tachyarrhythmia, it is determined whether the ventricular event falls within the region in which an atrial pacing event may obscure its detection. If not, then the VA interval is restarted as usual. However, if the ventricular event falls within this region, the VA interval is restarted with the VT rate detection boundary. This has the effect of lengthening the VA interval and the AA interval in this region so that atrial pacing events will not obscure the sensing and treatment of ventricular tachyarrhythmias in the region.

27 Claims, 12 Drawing Sheets

METHODS AND APPARATUS FOR TACHYCARDIA RATE HYSTERESIS FOR DUAL-CHAMBER CARDIAC STIMULATORS

CROSS REFERENCE TO RELATED APPLICATIONS

This application is a division of U.S. patent application Ser. No. 09/332,781, filed on Jun. 14, 1999, now issued as U.S. Pat. Ser. No. 6,233,485, the specification of which is incorporated herein by reference.

BACKGROUND OF THE INVENTION

1. Field of the Invention

The present invention relates generally to cardiac stimulators and, more particularly, to dual-chamber cardiac stimulators that have an improved ability to detect tachyarrhythmias.

2. Description of the Related Art

As most people are aware, the human heart is an organ having four chambers. A septum divides the heart in half, with each half having two chambers. The upper chambers are referred to as the left and right atria, and the lower chambers are referred to as the left and right ventricles. Deoxygenated blood enters the right atrium through the pulmonary veins. Contraction of the right atrium and of the right ventricle pump the deoxygenated blood through the pulmonary arteries to the lungs where the blood is oxygenated. This oxygenated blood is carried to the left atrium by the pulmonary veins. From this cavity, the oxygenated blood passes to the left ventricle and is pumped to a large artery, the aorta, which delivers the pure blood to the other portions of the body through the various branches of the vascular system.

In the normal human heart, the sinus node (generally located near the junction of the superior vena cava and the right atrium) constitutes the primary natural pacemaker by which rhyhnic electrical excitation is developed. The cardiac impulse arising from the sinus node is transmitted to the two atrial chambers. In response to this excitation, the atria contract, pumping blood from those chambers into the respective ventricles. The impulse is transmitted to the ventricles through the atrioventricular (AV) node to cause the ventricles to contract. This action is repeated in a rhythmic cardiac cycle in which the atrial and ventricular chambers alternately contract and pump, then relax and fill. One-way valves between the atrial and ventricular chambers in the right and left sides of the heart and at the exits of the right and left ventricles prevent backflow of the blood as it moves through the heart and the circulatory system.

The sinus node is spontaneously rhythmic, and the cardiac rhythm originating from the sinus node is referred to as sinus rhythm. This capacity to produce spontaneous cardiac impulses is called rhythmicity. Some other cardiac tissues also possess this electrophysiologic property and, hence, constitute secondary natural pacemakers. However, the sinus node is the primary pacemaker because it has the fastest spontaneous rate and because the secondary pacemakers tend to be inhibited by the more rapid rate at which impulses are generated by the sinus node.

The resting rates at which sinus rhythm occurs in normal people differ from age group to age group, generally ranging between 110 and 150 beats per minute ("bpm") at birth, and gradually slowing in childhood to the range between 65 and 85 bpm usually found in adults. The resting sinus rate, typically referred to simply as the "sinus rate," varies from one person to another and, despite the aforementioned usual adult range, is generally considered to lie anywhere between 60 and 100 bpm (the "sinus rate range") for the adult population.

A number of factors may affect the sinus rate, and some of those factors may slow or accelerate the rate sufficiently to take it outside of the sinus rate range. Slow rates (below 60 bpm) are referred to as sinus bradycardia, and high rates (above 100 bpm) are referred to as sinus tachycardia. In particular, sinus tachycardia observed in healthy people arises from various factors which may include physical or emotional stress, such as exercise or excitement, consumption of beverages containing alcohol or caffeine, cigarette smoking, and the ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from the normal sinus rate range. Arrhythmia rates which exceed the upper end of the sinus rate range are termed tachyarrhythmias. Healthy people usually experience a gradual return to their normal sinus rate after the removal of the factors giving rise to sinus tachycardia. However, people suffering from disease may experience abnormal arrhythmias that may require special, and in some instances immediate, treatment. In this text, we typically refer to abnormally high rates that have not yet been determined to be caused by myocardial malfunction as tachycardias and to abnormally high rates that have been determined to be caused by myocardial malfunction as tachyarrhythmias.

It should also be appreciated that an abnormal tachyarrhythmias may initiate fibrillation. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

In addition to rhythmicity, other electrophysiologic properties of the heart include excitability and conductivity. Excitability, which is the property of cardiac tissue to respond to a stimulus, varies with the different periods of the cardiac cycle. As one example, the cardiac tissue is not able to respond to a stimulus during the absolute refractory phase of the refractory period, which is approximately the interval of contraction from the start of the QRS complex to the commencement of the T wave of the electrocardiogram. As another example, the cardiac tissue exhibits a lower than usual response during another portion of the refractory period constituting the initial part of the relative refractory phase, which is coincident with the T wave. Also, the excitability of the various portions of the cardiac tissue differs according to the degree of refractoriness of the tissue.

Similarly, the different portions of the heart vary significantly in conductivity, which is a related electrophysiologic property of cardiac tissue that determines the speed with which cardiac impulses are transmitted. For example, ventricular tissue and atrial tissue are more conductive than AV junction tissue. The longer refractory phase and slower conductivity of the AV junction tissue give it a significant natural protective function, as described in more detail later.

For a variety of reasons, a person's heart may not function properly and, thus, endanger the person's well-being. Most typically, heart disease affects the rhythmicity of the organ, but it may also affect the excitability and/or conductivity of the cardiac tissue as well. As most people are aware, medical devices have been developed to facilitate heart function in such situations. For instance, if a person's heart does not beat properly, a cardiac stimulator may be used to provide relief. A cardiac stimulator is a medical device that delivers electrical stimulation to a patient's heart. A cardiac stimulator generally includes a pulse generator for creating electrical stimulation pulses and a conductive lead for delivering these electrical stimulation pulses to the designated portion of the heart. As described in more detail below, cardiac stimulators generally supply electrical pulses to the heart to keep the heart beating at a desired rate, although they may supply a relatively larger electrical pulse to the heart to help the heart recover from fibrillation.

Early pacemakers were devised to treat bradycardia. These pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy due to the constant pulse production. Even the sinus node of a heart in need of a pacemaker often provides suitable rhythmic stimulation occasionally. Accordingly, if a heart, even for a short period, is able to beat on its own, providing an electrical stimulation pulse using a pacemaker wastes the pacemaker's energy.

To address this problem, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval", the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 70 pulses per minute. To provide a more physiological response, pacemakers having a programmably selectable rate were developed. So long as the heart was beating above this programmably selected rate, the pacemaker did not provide any stimulation pulses. However, if the heart rate fell below this programmably selected rate, the pacemaker sensed the condition and provided stimulation pulses as appropriate.

Another major step in adding complexity and functionality to pacemakers occurred with the advent of pacemakers that had dual chamber capability. Dual chamber pacemakers are capable of sensing and/or pacing in two chambers, typically the right atrium and right ventricle. Accordingly, the distal ends of an atrial lead and a ventricular lead are coupled to the dual chamber pacemaker. The proximal end of the atrial lead is threaded through the pulmonary vein and into the right atrium of the heart. Similarly, the proximal end of the ventricular lead is threaded through the pulmonary vein, through the right atrium, and into the right ventricle of the heart. Each lead includes a mechanism on its proximal end that attaches to the inner wall of the heart to establish the required electrical connection between the pacemaker and the heart. Dual chamber pacemakers, as compared to single chamber pacemakers, typically function in a more physiologically correct manner.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient and alter the rate at which the stimulation pulses are provided to the heart. Typically, this monitored physiological parameter relates to the changing physiological needs of the patient. For instance, when a person is at rest, the person's heart need only beat relatively slowly to accommodate the person's physiological needs. Conversely, when a person is exercising, the person's heart tends to beat rather quickly to accommodate the person's heightened physiological needs.

Unfortunately, the heart of a person in need of a pacemaker may not be able to beat faster on its own. Prior to the development of rate-responsive pacemakers, patients were typically advised to avoid undue exercise, and pacemaker patients that engaged in exercise tended to tire quickly. Rate-responsive pacemakers help relieve this constraint by sensing one or more physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

As noted above, pacemakers have historically been employed primarily for the treatment of heart rates which are unusually slow, i.e., bradyarrhythmias. However, over the past several years cardiac pacing has found significantly increasing usage in the management of heart rates which are unusually fast, i.e., tachyarrhythmias. Anti-tachyarrhythmia pacemakers take advantage of the previously mentioned inhibitory mechanism that acts on the secondary natural pacemakers to prevent their spontaneous rhymicity, sometimes termed "postdrive inhibition" or "overdrive inhibition". In essence, the heart may be stimulated with a faster than normal pacing rate (1) to suppress premature atrial or ventricular contractions that might otherwise initiate ventricular tachycardia, flutter (a tachyarrhythmia exceeding 200 bpm), or fibrillation or (2) to terminate an existing tachyarrhythmia.

Typically, these pulses need only be of sufficient magnitude to stimulate the excitable myocardial tissue in the immediate vicinity of the pacing electrode. However, another technique for terminating tachyarrhythmias, referred to as cardioversion, utilizes apparatus to shock the heart synchronized to the tachyarrhythmia with one or more current or voltage pulses of considerably higher energy content than that of the pacing pulses. Defibrillation, a related technique, also involves applying one or more high energy "countershocks" to the heart in an effort to overwhelm the chaotic contractions of individual tissue sections to allow reestablishment of an organized spreading of action potential from cell to cell of the myocardium and, thus, restore the synchronized contraction of the mass of tissue.

In the great majority of cases, atrial fibrillation is hemodynamically tolerated and not life-threatening because the atria provide only a relatively small portion (typically on the order of 15 to 20 percent) of the total volume of blood pumped by the heart per unit time, typically referred to as cardiac output. During atrial fibrillation, the atrial tissue remains healthy because it is continuing to receive a fresh supply of oxygenated blood as a result of the continued pumping action of the ventricles. Atrial tachyarrhythmia may also be hemodynamically tolerated because of the natural protective property of the junctional tissue attributable to its longer refractory period and slower conductivity than atrial tissue. This property renders the junctional tissue unable to respond fully to the more rapid atrial contractions. As a result, the ventricle may miss every other, or perhaps two of every three, contractions in the high rate atrial sequence, resulting in 2:1 or 3:1 A-V conduction and, thus, maintain relatively strong cardiac output and an almost normal rhythm.

Nevertheless, in cases where the patient is symptomatic or at high risk in events of atrial tachyarrhythmia or fibrillation, special treatment of these atrial disorders may be appropriate. Such circumstances may include, for example, instances where the patient suffers from ventricular heart disease and cannot easily withstand even the small consequent reduction of ventricular pumping capability, as well as instances where the rapid atrial rhythm is responsible for an excessively rapid ventricular rate. The methods of treatment commonly prescribed by physicians for treating atrial tachyarrhythmia and fibrillation include medication, catheter ablation, pacing therapy, cardiac shock therapy, and in some cases, surgically creating an A-V block and implanting a ventricular pacemaker.

In contrast to the atrial arrhythmias discussed above, cardiac output may be considerably diminished during an episode of ventricular tachyarrhythmia because the main pumping chambers of the heart, the ventricles, are only partially filled between the rapid contractions of those chambers. Moreover, ventricular tachyarrhythmia can present a risk of acceleration of the arrhythmia into ventricular fibrillation. As in the case atrial fibrillation, ventricular fibrillation is characterized by rapid, chaotic electrical and mechanical activity of the excitable myocardial tissue. However, in contrast to atrial fibrillation, ventricular fibrillation manifests an instantaneous cessation of cardiac output as the result of the ineffectual quivering of the ventricles—a condition that typically requires almost immediate treatment.

Conventional cardiac stimulators monitor the ventricular rate to determine the nature of an arrhythmia. When a ventricular tachyarrhythmia is detected, the cardiac stimulator delivers anti-tachyarrhythmia pacing therapy to the ventricle or a higher level shock to the ventricle.

More recently, there has been a combination of certain complementary technologies, namely the combination of anti-tachycardia pacemakers with dual-chamber rate-responsive pacemakers. Generally speaking, a dual-chamber rate-responsive anti-tachycardia pacemaker offers improved performance over the pacemakers discussed above. However, pacemakers of this type exhibit certain disadvantages which are described below along with certain exemplary methods and apparatus directed to addressing these disadvantages.

SUMMARY OF THE INVENTION

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

During the operation of a cardiac stimulator, it is generally desirable that the pacing not delay the detection of a tachyarrhythmia In conventional cardiac stimulators, such as some of those described above, this function is accomplished by providing discreet rate zones for tachyarrhythmia detection and bradyarrhythmia treatment, where the fastest demand pacing rate is less than the slowest tachyarrhythmia detection rate. As a result, the shortest pacing interval will always be longer than the longest tachyarrhythmia interval. Thus, this ensures that a detected ventricular event will not be followed by a demand pace, which may obscure a tachyarrhythmia event, until the longest possible interval for tachyarrhythmia detection has expired. While this functionality works well for cardiac stimulators which pace in the ventricle only, it has been discovered that such functionality could obscure certain tachyarrhythmia events in dual-chambered cardiac stimulators, primarily because the atrial pacing may also obscure the detection of tachyarrhythmia events.

As described in detail below with respect to the disclosed embodiments, in a conventional dual-chambered cardiac stimulator using such conventional functionality, there is a region where a ventricular tachyarrhythmia may exceed the tachyarrhythmia detection rate boundary in a region where the VA interval is shorter than the VT interval. Thus, detection of the ventricular tachyarrhythmia in this region causes the VA interval to be restarted so that an atrial demand pace would be delivered at the end of the VA interval. Therefore, there is a possibility that this atrial demand pace will obscure the subsequent ventricular tachyarrhythmia sensing and, thus, potentially delay detection of a ventricular tachyarrhythmia.

To address this situation, a number of techniques are described in detail below. In accordance with one technique, it is determined whether a ventricular event should be classified as a ventricular tachyarrhythmia. If not, the VA interval is restarted as usual. However, if the ventricular event may be classified as a ventricular tachyarrhythmia, it is determined whether the ventricular event falls within the region in which an atrial pacing event may obscure its detection. If not, then the VA interval is restarted as usual. However, if the ventricular event falls within this region, the VA interval is restarted with the VT rate detection boundary. This has the effect of lengthening the VA interval and the AA interval in this region so that atrial pacing events will not obscure the sensing and treatment of ventricular tachyarrhythmias in the region.

This technique may be modified by using a tachycardia rate different than the ventricular tachycardia rate detection boundary. For example, a tachycardia rate may be selected between well tolerated tachyarrhythmias and moderately tolerated tachyarrhythmias so that the VA interval and the AA interval are lengthened only when ventricular events fall within an upper portion of the previously discussed region. Although the well tolerated ventricular tachyarrhythmias may be obscured by atrial pacing events using this technique, the more clinically significant tachyarrhythmias will not be obscured.

In another modification of the previously discussed technique, it is determined whether a ventricular event should be classified as a ventricular tachyarrhytia If not, the VA interval is restarted as usual. However, if the ventricular event may be classified as a ventricular tachyarrhythmia, the VA interval is restarted with the VT rate detection boundary, and the VA interval is extended so that the AA interval does not exceed the maximum pacing rate. This technique has the effect of lengthening the AA interval, and thus lowering the pacing rate, only to the extent required to prevent an atrial pacing event from obscuring a ventricular tachyarrhythmia.

Finally, the programmable ranges of various parameters may be restricted to reduce or eliminate the circumstance in which an atrial pacing event may obscure a ventricular tachyarrhythmia. For instance, the VT rate detection boundary may be set higher than the VA interval so that ventricular events classified as ventricular tachyarrhythmias are always faster Man the VA interval. Also, the maximum pacing rate may be reduced so that the resulting VA interval is raised above the VT interval in the region above the VT rate detection boundary. Further, the AV interval may be reduced in the region to effectively raise the VA interval above the VT interval in the region above the VT rate detection boundary. Indeed, various combinations of these three restriction techniques may be used to program the cardiac stimulator to best fit a particular patient's needs while minimizing the region in which ventricular tachyarrhythmias may be obscured by an atrial pacing event.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
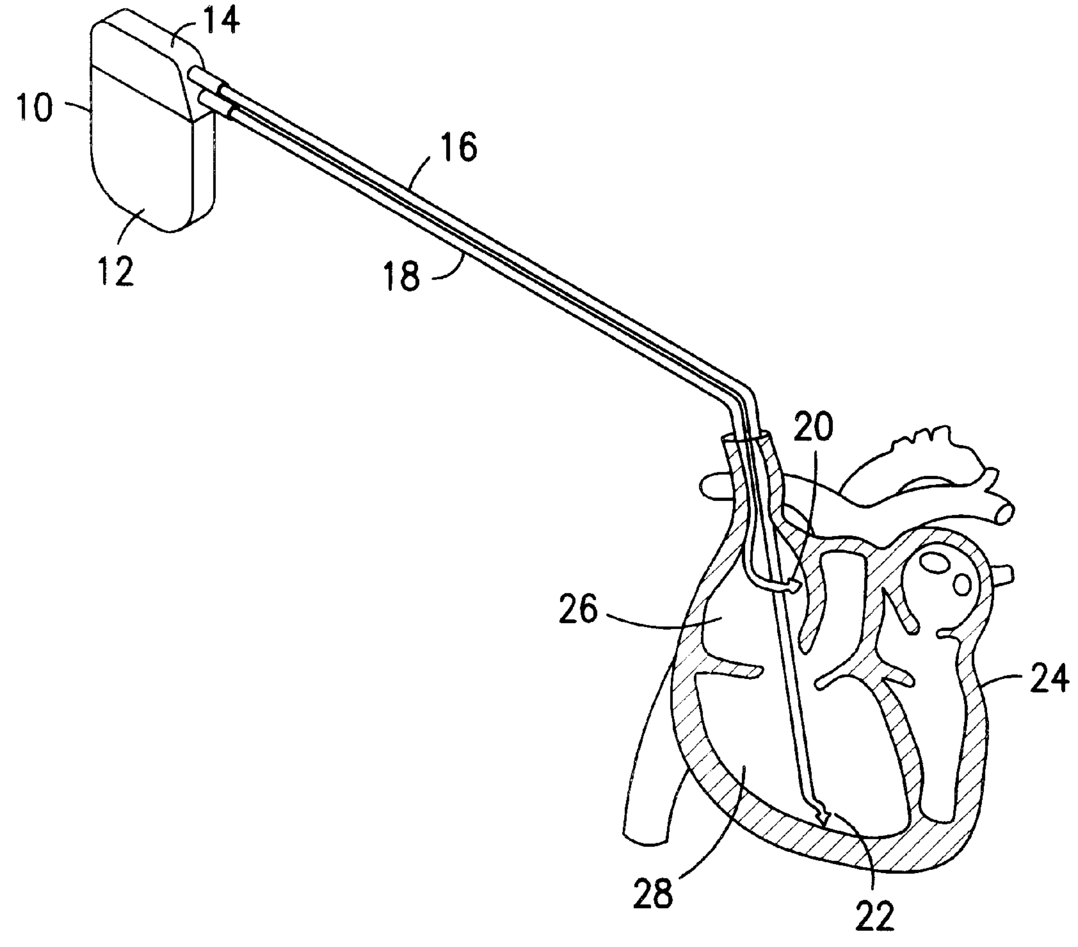
FIG. 1 illustrates a cardiac stimulator having two leads coupled to a patient's heart.

Turning now to the drawings, and referring initially to FIG. 1, one embodiment of a dual-chamber cardiac stimulator is illustrated and generally designated by the reference numeral 10. As discussed below, the cardiac stimulator 10 may include an apparatus for adjusting basic time intervals versus rate to enhance the ability of the cardiac stimulator 10 to detect tachyarrhythmias. The general structure and operation of the cardiac stimulator 10 will be discussed with respect to FIGS. 1–3. Then, the functioning of a conventional dual-chamber cardiac stimulator will be discussed with regard to FIGS. 4 and 5 in order to highlight certain circumstances that may mask or delay tachyarrhythmia detection. Once these circumstances have been described, various exemplary methods for addressing these circumstances will be described with reference to FIGS. 6–13.

As shown in FIG. 1, the body of the cardiac stimulator 10 includes a case 12 and a header 14. The cardiac stimulator 10 may be implantable or non-implantable. If implantable, the case 12 and the header 14 are hermetically sealed to prevent bodily fluids from damaging the internal circuitry of the cardiac stimulator 10. Typically, the case 12 is made of titanium, and the header 14 is made of polyethylene.

In the described embodiment, the cardiac stimulator 10 is a dual chamber cardioverter/defibrillator (ICD), although it should be understood that the teachings set forth herein may apply to other types of cardiac stimulators. Because the cardiac stimulator 10 is a dual chamber ICD, it includes an atrial lead 16 and a ventricular lead 18. Typically, the leads 16 and 18 are generally flexible and include an electrically conductive core surrounded by a protective sheath. For instance, the internal core may be a coiled copper wire, and the protective sheath may be a coating of polyethylene.

Each lead 16 and 18 includes a respective tip 20 and 22 that is designed to be implanted or coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

Figure 2:
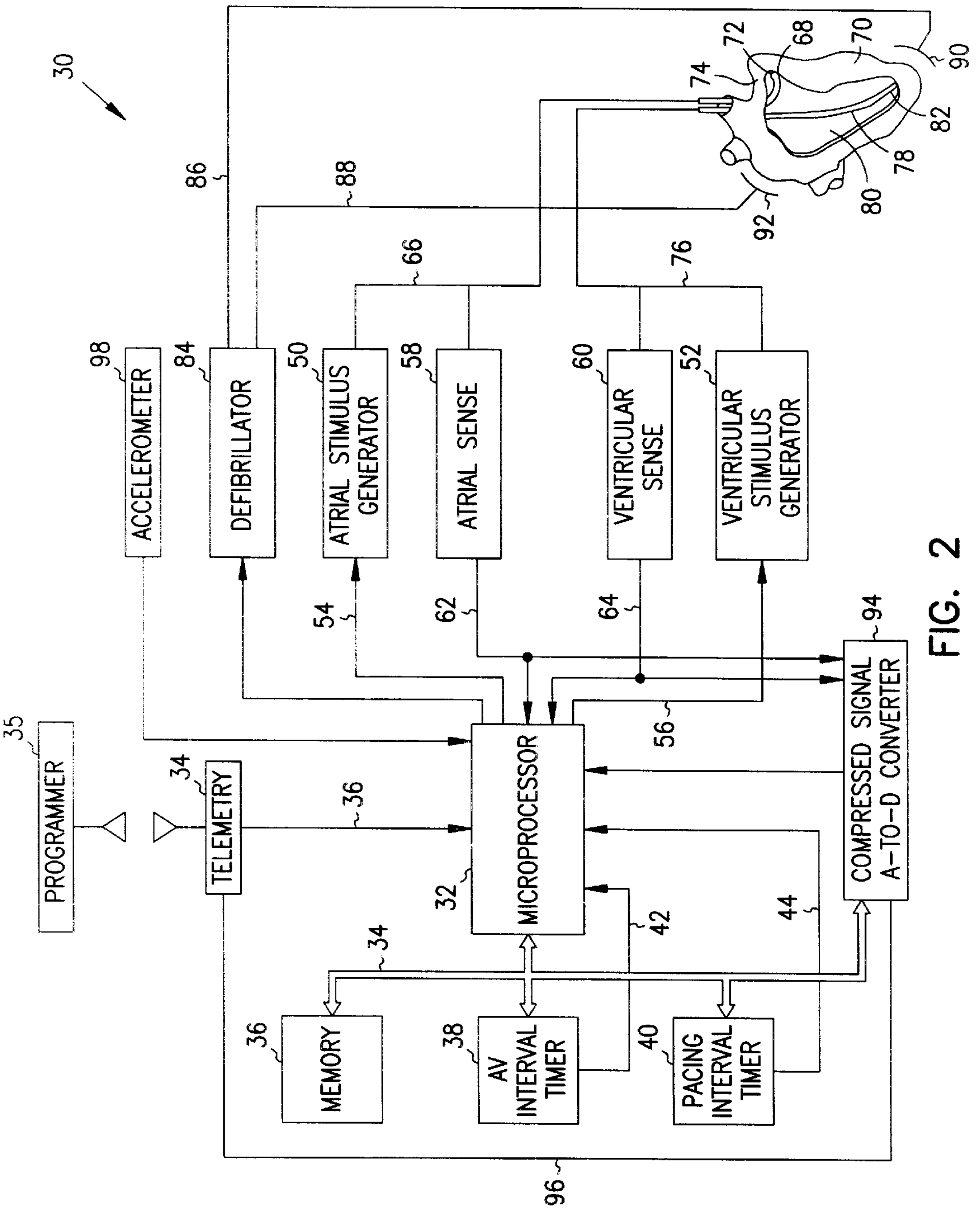
FIG. 2 illustrates a block diagram of an exemplary cardiac stimulator.

The cardiac stimulator 10 uses electronic circuitry to perform its functions, such as the circuitry illustrated in FIG. 2 and generally designated by the reference numeral 30. A microprocessor 32 provides pacemaker control and computational facilities. Although it will be appreciated that other forms of circuitry, such as analog or discrete digital circuitry, can be used in place of microprocessor 32, a microprocessor is typically advantageous due to its miniature size and its flexibility. A particularly energy efficient microprocessor, which is designed specifically for use in pacemakers, is fully described in U.S. Pat. Nos. 4,390,022 and 4,404,972, which are assigned to the assignee of my invention.

The microprocessor 32 has input/output ports connected in a conventional manner via bidirectional bus 34 to memory 36, an AV interval timer 38, and a pacing interval timer 40. In addition, the AV interval timer 38 and pacing interval timer 40 each has an output connected to a corresponding input port of the microprocessor 32 by lines 42 and 44 respectively. Memory 36 may include both ROM and RAM, and the microprocessor 32 may also contain additional ROM and RAM. The pacemaker operating routine is typically stored in ROM, while the RAM stores programmable parameters and variables in conjunction with the pacemaker operation.

The AV and pacing interval timers 38 and 40 may be external to the microprocessor 32, as illustrated, or internal thereto. The timers 38 and 40 may be, for instance, suitable conventional up/down counters of the type that are initially loaded with a count value and count up to or down from the value and output a rollover bit upon completing the programmed count. The initial count value is loaded into the timers 38, 40 on bus 34 and the respective rollover bits are output to the microprocessor 32 on lines 42 and 44.

The microprocessor 32 typically also has an input/output port connected to a telemetry interface 46 by line 48. The pacemaker, when implanted, is thus able to receive pacing and rate control parameters from an external programmer 35 and to send data to an external receiver if desired. Many suitable telemetry systems are known to those skilled in the art. One such system and encoding arrangement is described in U.S. Pat. No. 4,539,992, which is also assigned to the assignee of my invention.

The microprocessor output ports are connected to inputs of an atrial stimulus pulse generator 50 and a ventricular stimulus pulse generator 52 by control lines 54 and 56, respectively. The microprocessor 32 transmits pulse parameter data, such as amplitude and width, as well as enable/disable and pulse initiation codes to the generators 50, 52 on the respective control lines. The microprocessor 32 also has input ports connected to outputs of an atrial sense amplifier 58 and a ventricular sense amplifier 60 by lines 62 and 64 respectively. The atrial and ventricular sense amplifiers 58, 60 detect occurrences of P-waves and R-waves respectively.

The input of the atrial sense amplifier 58 and the output of the atrial stimulus pulse generator 50 are connected to a first conductor 66 which is inserted in a first conventional lead 68. Lead 68 is inserted into a heart 70 intravenously or in any other suitable manner. The lead 66 has an electrically conductive pacing/sensing tip 72 at its distal end which is electrically connected to the conductor 66. The pacing/sensing tip 72 is typically lodged in the right atrium 74.

The input of the ventricular sense amplifier 60 and the output of the ventricular stimulus pulse generator 52 are connected to a second conductor 76. The second conductor 76 is inserted in a second conventional lead 78 which is inserted intravenously or otherwise in the right ventricle 80 of the heart 70. The second lead 78 has an electrically conductive pacing/sensing tip 82 at its distal end. The pacing/sensing tip 82 is electrically connected to the conductor 76. The pacing/sensing tip 82 is typically lodged on the wall of the right ventricle.

The conductors 50, and 52 conduct the stimulus pulses generated by the atrial and ventricular stimulus pulse generators 66, 76, respectively, to the pacing/sensing tips 72, 82. The pacing/sensing tips 72, 82 and corresponding conductors 66, 76 also conduct sensed cardiac electrical signals in the right atrium and right ventricle to the atrial and ventricular sense amplifiers 58, 60.

In addition, it may be desired to provide defibrillation capability in the cardiac stimulator 10. if this is the case, a high voltage defibrillator circuit 84 is provided which is controlled by the microprocessor 32. The defibrillator circuit 84 is connected to heart tissue through two high voltage leads 86, 88 which communicate with the heart through electrodes 90, 92. In the illustrated embodiment, epicardial patch electrodes are diagrammatically represented. However, other electrode configurations, including endocardial electrodes, may also be suitable.

The atrial and ventricular sense amplifiers 58, 60 communicate both with the microprocessor and with a compressed signal A-to-D converter 94. The compressed signal A-to-D converter 94 communicates through the bus 34 with memory 36 and the microprocessor 32, primarily, and on a line 96 with the telemetry 46. Thus, the output of the converter 94 can be manipulated by the microprocessor 32, or stored in memory 36 or directly communicated through the telemetry 46 to the programmer 35. The stored output of the convertor 94 may also be subsequently communicated from memory 36 through the telemetry 46 to the program 35.

The microprocessor 32 may also base its control on other parameters, such as information received from other sensors. For example, an activity sensor 98, such as an implanted accelerometer, may be used to gather information relating to changing environmental or physiological conditions. Although the use of an accelerometer as the activity sensor 98 may be advantageous, other types of sensors may also be used to gauge certain types of physical activity or physical condition, such as vibration sensors, temperature sensors, oxygen sensors, pH sensors, and/or impedance sensors. Indeed, when the dual-chamber cardiac stimulator 10 is operating in rate-responsive mode, the stimulator 10 typically adjusts the pacing rate in response to one or more detected physiological or environmental parameters conrelated to a physiologic need.

Figure 3:
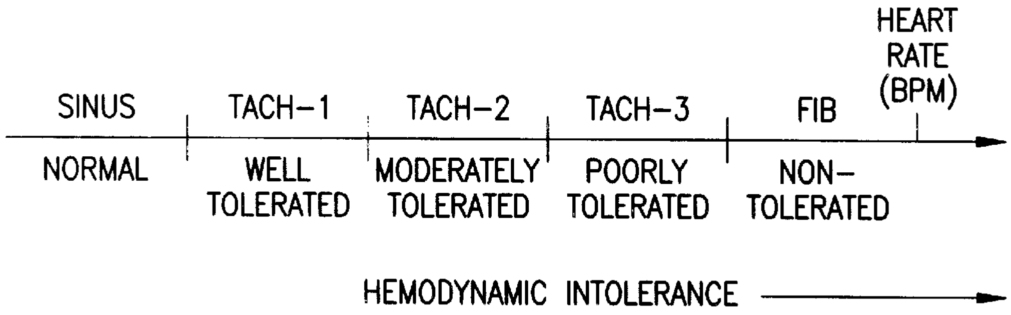
FIG. 3 illustrates a diagram of a typical heart rate spectrum that illustrates programmable rates at the boundaries of each arrhythmia class.

The operation of the cardiac stimulator 10 may be affected by heart rate. With reference now to FIG. 3, a heart rate spectrum may be stored in the circuitry 30 and partitioned into a multiplicity of regions defining contiguous, successive heart rate ranges. At the lower end of the illustrated heart rate spectrum is normal rhythm, which is designated SINUS. As the heart rate rises along the spectrum, the spectrum enters progressively higher rate ranges associated with ventricular tachycardia or tachyarrhythmia, respectively labeled TACH-1, TACH-2, and TACH-3. Beyond the ventricular tachycardia ranges of the spectrum lies the range associated with ventricular fibrillation, which is labeled FIB.

It will be observed that the spectrum may be partitioned such that the rate ranges are representative of respective degrees of hemodynamic tolerance of the patient to cardiac rates in those regions. Generally speaking, heart rates in the SINUS region are normal, whereas rates in the FIB region cannot be tolerated. Furthermore, the ascending order of the three illustrated ventricular tachyarrhythmia regions TACH-1, TACH-2, and TACH-3 depicts well tolerated, moderately tolerated, and poorly tolerated classes of tachycardia, respectively. Although tree tachyarrhythmia classes are illustrated, the actual number of such classes may be greater or fewer depending on the judgment of the physician regarding the management of anthymias and the prescription of therapy regimens for a particular patient. As will become clear from the discussion of therapy considerations below, the number of tachyarrhythmia classes is of less concern than the relationship between the maximum pacing rate and the tachyarrhythmia detection rate boundary. In the examples discussed below, it will be assumed that the end of the SINUS range represents the maximum pacing rate of the cardiac stimulator 10 and that the beginning of the TACH-1 range represents the detection rate boundary for ventricular tachyarrhythmias.

Figure 4:
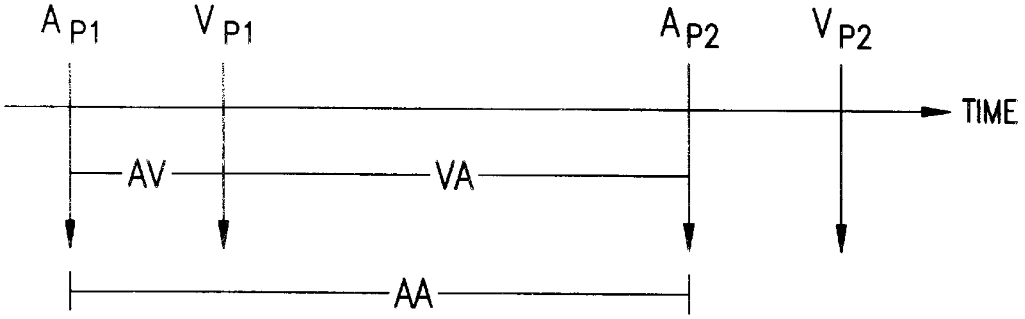
FIG. 4 illustrates a timing diagram of exemplary atrial and ventricular events.
Figure 5:
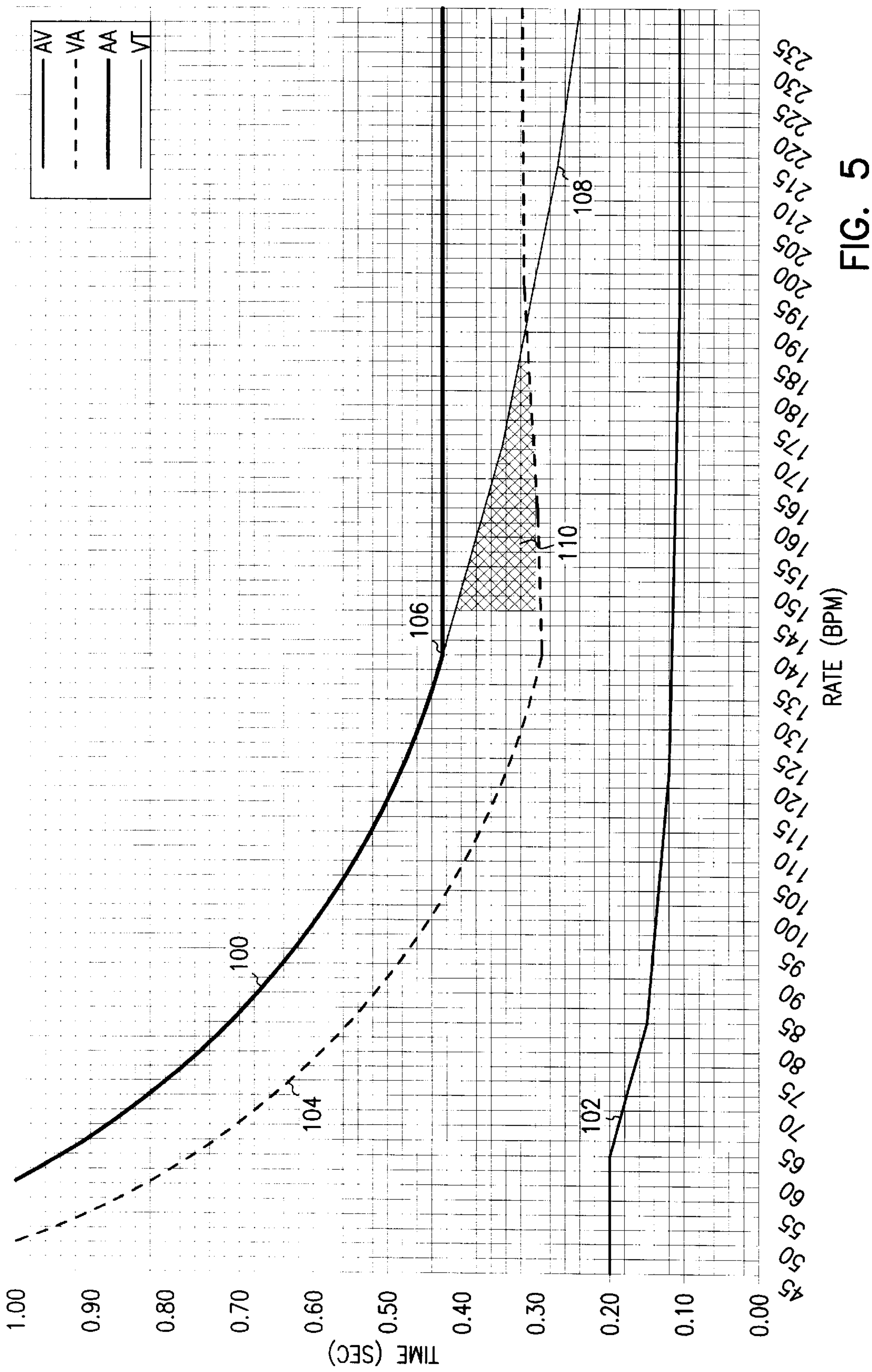
FIG. 5 illustrates a graphical representation of basic time intervals versus rate occurring within a conventional dual-chamber cardiac stimulator.

As illustrated in FIG. 4, the pacing rate is determined by the time interval between an atrial pace or sensed P-wave $A_{p1}$ until a successive atrial pace event $A_{p2}$. Thus, the pace interval AA, which is illustrated in FIG. 5 as curve 100, essentially defines the pacing rate of the cardiac stimulator 10. After the first atrial pace event $A_{p1}$, a ventricular pace event $V_{p1}$ occurs. The time interval between the atrial pace event $A_{p1}$ and the ventricular pace event $V_{p1}$ is defined as the AV interval, which is illustrated in FIG. 5 as curve 102. After the ventricular pace event $V_{p1}$ a time interval VA extends from the ventricular pace event $V_{p1}$ to the next atrial pace event $A_{p2}$. The curve 104 of FIG. 5 illustrates an example of a VA interval. It should be noted that the AV interval when combined with the VA interval equals the AA interval, e.g., the pacing rate.

Referring to FIG. 5, it should be noted that the AV interval curve 102 is an adaptive function used in dual-chamber cardiac stimulators, where the AV interval decreases from its programmed value, e.g., 200 milliseconds, when the atrial rate exceeds a threshold, e.g., 60 BPM, with a decrease of 1 millisecond for every 8 milliseconds decrease in atrial rate. Of course, the AV interval curve 102 could also be illustrated as a constant value. It should also be noted that the AA interval curve 100 is, as mentioned above, the sum of the AV interval and the VA interval, although it should be further understood that the VA interval is typically adjusted by the cardiac stimulator to maintain the desired AA interval based upon changes in the AV interval.

As shown by the AA interval curve 100, the cardiac stimulator in this example begins delivering pacing pulses at about 65 BPM. Because the cardiac stimulator is rate responsive, the pacing rate may continue to increase until it reaches a maximum pacing rate, which is illustrated at point 106 as about 140 BPM in this example. Since ventricular tachycardia (VT) detection zones are generally restricted to be above the MPR, as discussed previously, a VT interval-versus-rate curve 108 is illustrated to begin at about 150 BPM in this example.

From FIG. 5 it can be seen that if a ventricular tachycardia exceeds the detection rate boundary of 150 BPM, there is a region where the VT interval curve 108 exceeds the VA interval curve 104 and forms, in this example, a triangle 110 between 150 BPM and approximately 190 BPM. In this region, if a ventricular tachycardia R-wave were sensed, the VA interval would be restarted and an atrial demand pace would be delivered at the end of the VA interval. However, since the VA interval in this region was shorter than the VT interval, the ventricular tachycardia may occur during the AV interval. In this situation, the atrial demand pace $A_p$ may obscure the ventricular tachycardia R-wave and, thus, potentially delay detection of the ventricular tachycardia. Furthermore, if the atrial pace $A_p$ is followed by a ventricular pace $V_p$ (because the ventricular tachycardia R-wave was obscured), the ventricular pace may occur in a physiologically vulnerable period. Of course, if the ventricular tachycardia exceeds the rate of 190 BPM, the VT interval is less than the VA interval, so the next ventricular tachycardia event would be sensed prior to the next atrial pace $A_p$.

In view of the above discussion of FIG. 5, it would be desirable to improve the ability of a dual-chamber cardiac stimulator to detect tachyarrhythmias, particularly tachyarrhythmias that are at or only marginally above the detection rate boundary. One technique for addressing this problem is described in reference to FIGS. 6 and 7. These figures describe a technique that adds "tachycardia hysteresis" to the atrial pacing rate to prevent obscuring ventricular tachyarrhytmias under atrial pacing.

Figure 6:
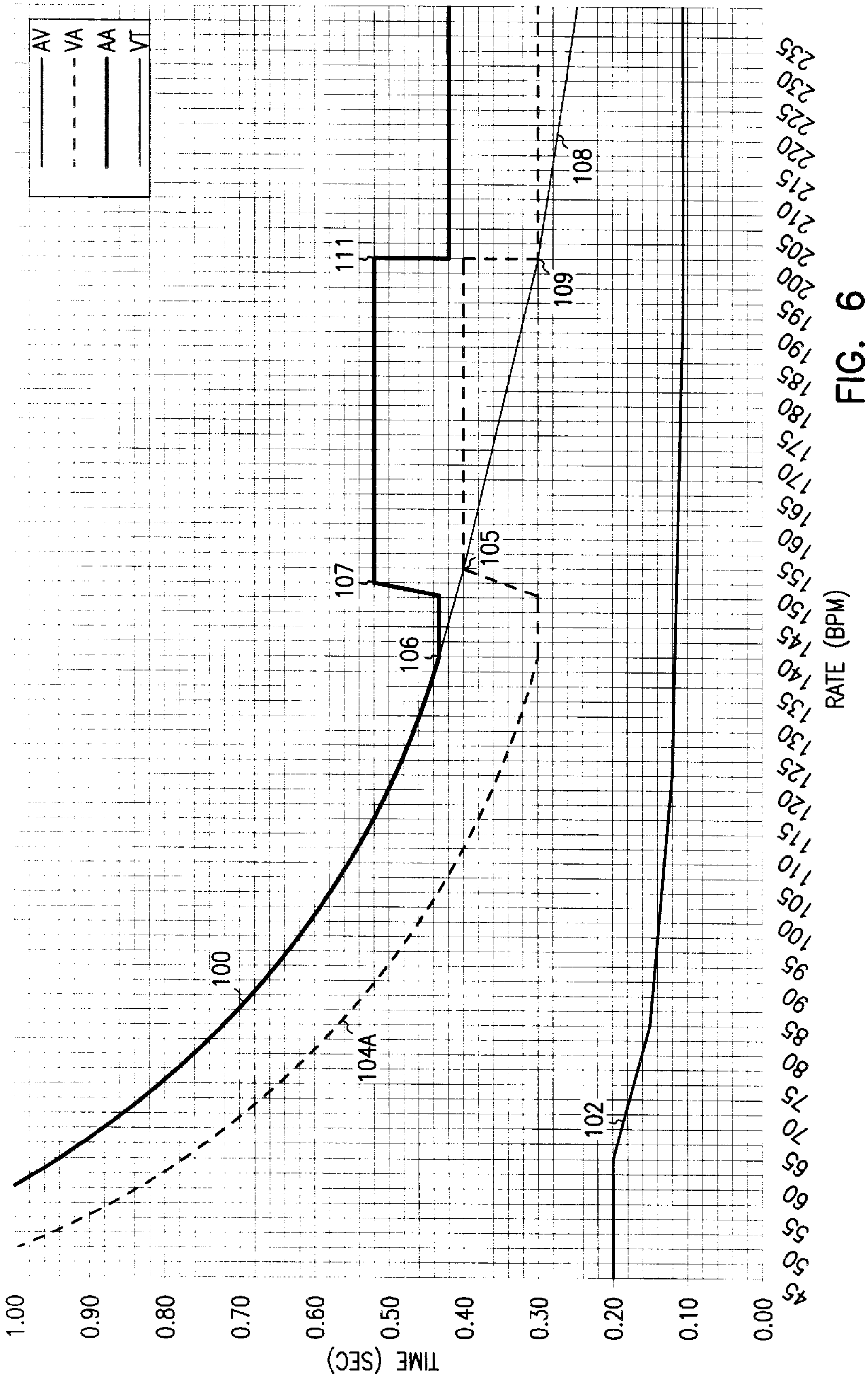
FIG. 6 illustrates a graphical representation of basic time intervals versus rate for a dual-chamber cardiac stimulator in accordance with the present invention.

To carry forward the example illustrated in FIG. 5, it should be noted that identical or similar reference numerals and the same MPR and tachycardia rate detection boundary are used in FIG. 6. In particular, it should be noted that the AV interval curve 102 and the VT interval curve 108 are the same in this example as in the example illustrated in FIG. 5. However, it should be noted that the VA interval curve 104A is skewed upwardly at about the VT rate detection boundary of 150 BPM, as illustrated by the point 105. Indeed, as illustrated by the VA interval curve 104A in FIG. 6, the VA interval is lengthened at about the VT rate detection boundary to make it equal to or greater than the longest VT interval illustrated by the VT interval curve 108. Due to the additive effects of the AV interval curve 102 and the VA interval curve 104A, this action effectively increases the AA interval at point 107, and thus reduces the atrial pacing rate, slightly in the presence of high rate ventricular activity. Thus, it should be noted that the AA interval curve 100A skews upwardly in a manner similar to that of the VA interval curve 104A. It should also be noted that this action removes the triangle 110. Once the ventricular activity rises above about 190 BPM, the VA curve 104A and the AA curve 100A drop back to previous levels at points 109 and 111, respectively.

Figure 7:
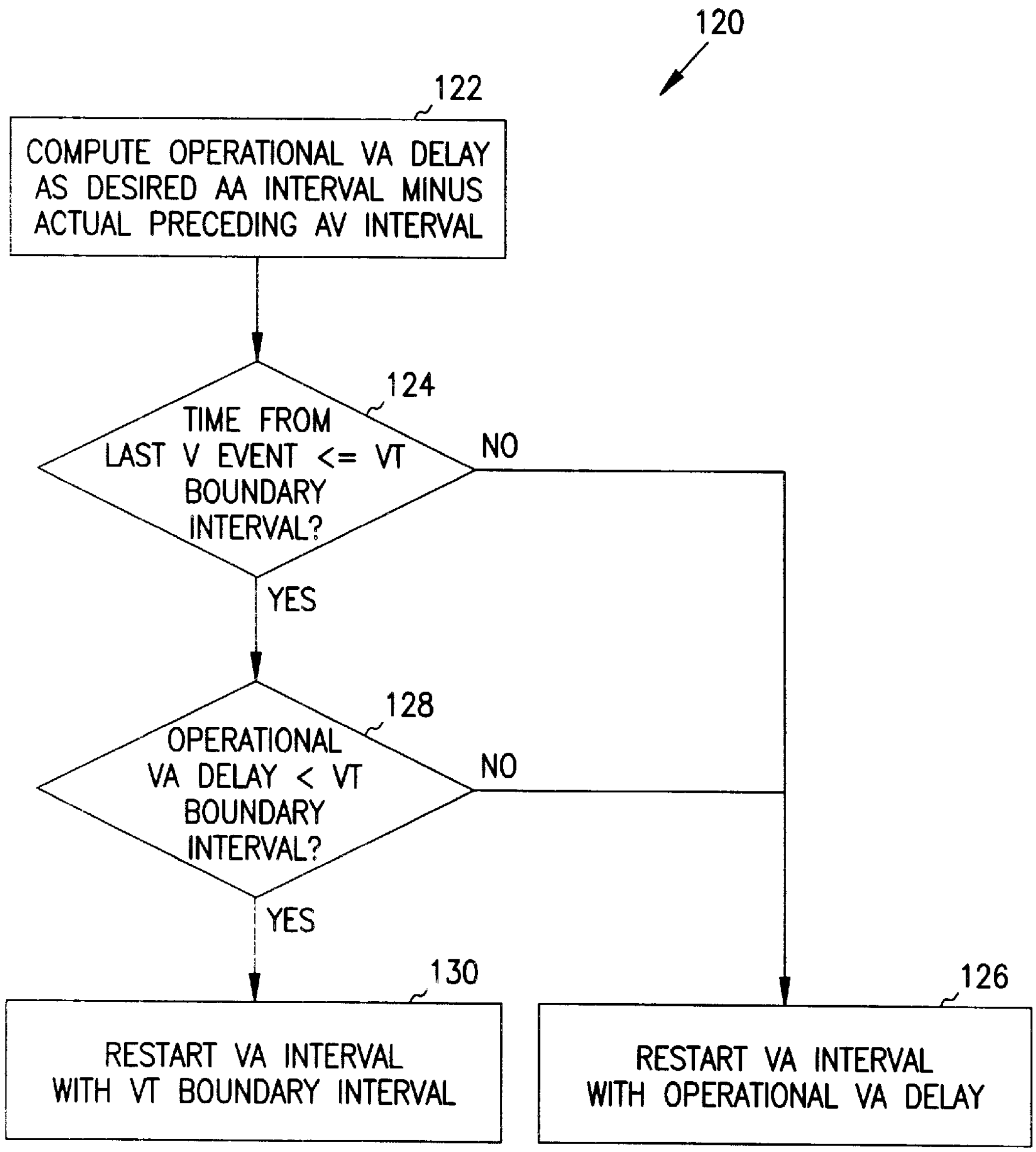
FIG. 7 illustrates a flow chart depicting the functioning of a dual-chamber cardiac stimulator in accordance with FIG. 6.

Referring additionally to FIG. 7, when any ventricular event is detected at or above the VT rate detection boundary, the VA interval is restarted with the larger of the VT boundary interval or the operational VA delay. The operational VA delay is defined as the desired AA interval minus the actual proceeding AV interval. In a specific example illustrated in the flow chart 120, when a ventricular event at or above the VT rate detection boundary is detected, the operational VA delay is computed. (Block 122). It is then determined whether the time from the last ventricular event, i.e., the VV interval, is less than or equal to the VT boundary interval. (Block 124). If the VV interval is less than or equal to the VT rate detection boundary, the detected ventricular event is not a ventricular tachycardia Therefore, the cardiac stimulator continues to operate in the region of the graph to the left of the MPR 106. Accordingly, the VA interval is restarted with the operational VA delay as illustrated in both FIGS. 5 and 6. (Block 126).

However, if the VV interval is greater than the VT rate detection boundary, then the ventricular event is indicative of a ventricular tachyarrhythmia. Thus, the cardiac stimulator begins to operate in the region of the graph of FIG. 6 to the right of the MPR 106. To determine how to restart the VA interval, it is next determined whether the operational VA delay is less than the VT rate detection boundary. (Block 128). If not, then the VT interval is less than the VA interval so that the ventricular event essentially falls within the portion of the graph illustrated in FIG. 5 to the right of the triangle 110. Because, in this region, another ventricular event will appear before an atrial pace can be delivered, the VA interval may be restarted with the operational VA delay. (Block 126). Thus, the cardiac stimulator 10 operates to the right of the points 109 and 111 illustrated in FIG. 6.

On the other hand, if the operational VA delay is less than the VT rate detection boundary, the ventricular event falls within the triangle 110 of FIG. 5, e.g., the ventricular event is in the range of approximately 150 BPM to 190 BPM in this example. Because, as described above, a ventricular tachycardia in this range may escape detection using the scheme set forth in FIG. 5, the VA interval is restarted with the VT boundary interval. (Block 130). As mentioned earlier, this action essentially moves the VA curve 104A upwardly to the VT boundary rate interval. This action has the effect of slowing the pacing rate, as evidence by the similarly displaced AA interval curve 100A, so that atrial pacing events are precluded until the ventricular tachycardia may be sensed and treated.

One advantage of this approach is that it prevents atrial pacing from obscuring the detection of ventricular tachycardia without the constraints of limiting the cardiac stimulator's programmable parameter ranges. Furthermore, the decision set forth in Block 124 offers the advantage of applying tachycardia hysteresis only when the ventricular activity indicates a potential ventricular tachycardia, so that tachycardia hysteresis is not applied to slower ventricular events which would effectively reduce the MPR. Also, the decision set forth in Block 128 ensures that on cycles with a very short AV interval and a resulting long operational VA interval (longer than the VT interval), the MPR will not be exceeded. Finally, the restarting process set forth in Block 130 provides a mechanism for tachyarrhythmia hysteresis that allows ventricular tachyarrhythmia detection by extending the pacing rate.

While the technique described with respect to FIGS. 6 and 7 clearly offers many advantages, it should be understood that the technique may be altered in various ways. For example, as mentioned much earlier with respect to FIG. 3, the cardiac stimulator 10 may be programed with multiple rate boundaries that define a plurality of different tachyarrhythmia ranges. For example, as illustrated in FIG. 3, the TACH-1 range defines a range in which tachyarrhythmias may be well tolerated by the patient. In such a circumstance, the technique described in reference to FIGS. 6 and 7 may be modified to replace the VT rate detection boundary with the boundary between the TACH-1 and TACH-2 ranges, which in this example may be 175 BPM. By referring to FIG. 8, it can be seen by references to curves 100B and 104B that this action causes less fluctuation in the MPR in the portion of the graph to the right of the point 106 as compared with the technique described with reference to FIGS. 6 and 7. Disadvantageously, however, it should also be noted that there exists a region between about 150 BPM and about 175 BPM, as illustrated by the triangle 110A, where an atrial pace event could obscure a ventricular tachyarrhythmia However, as stated previously, if ventricular tachyarrhythmias in this range are well tolerated by the patient, the fact that some of these ventricular events remain undetected should not pose any problems for the patient, while allowing the cardiac stimulator 10 to operate in a more physiologically correct manner.

Figure 8:
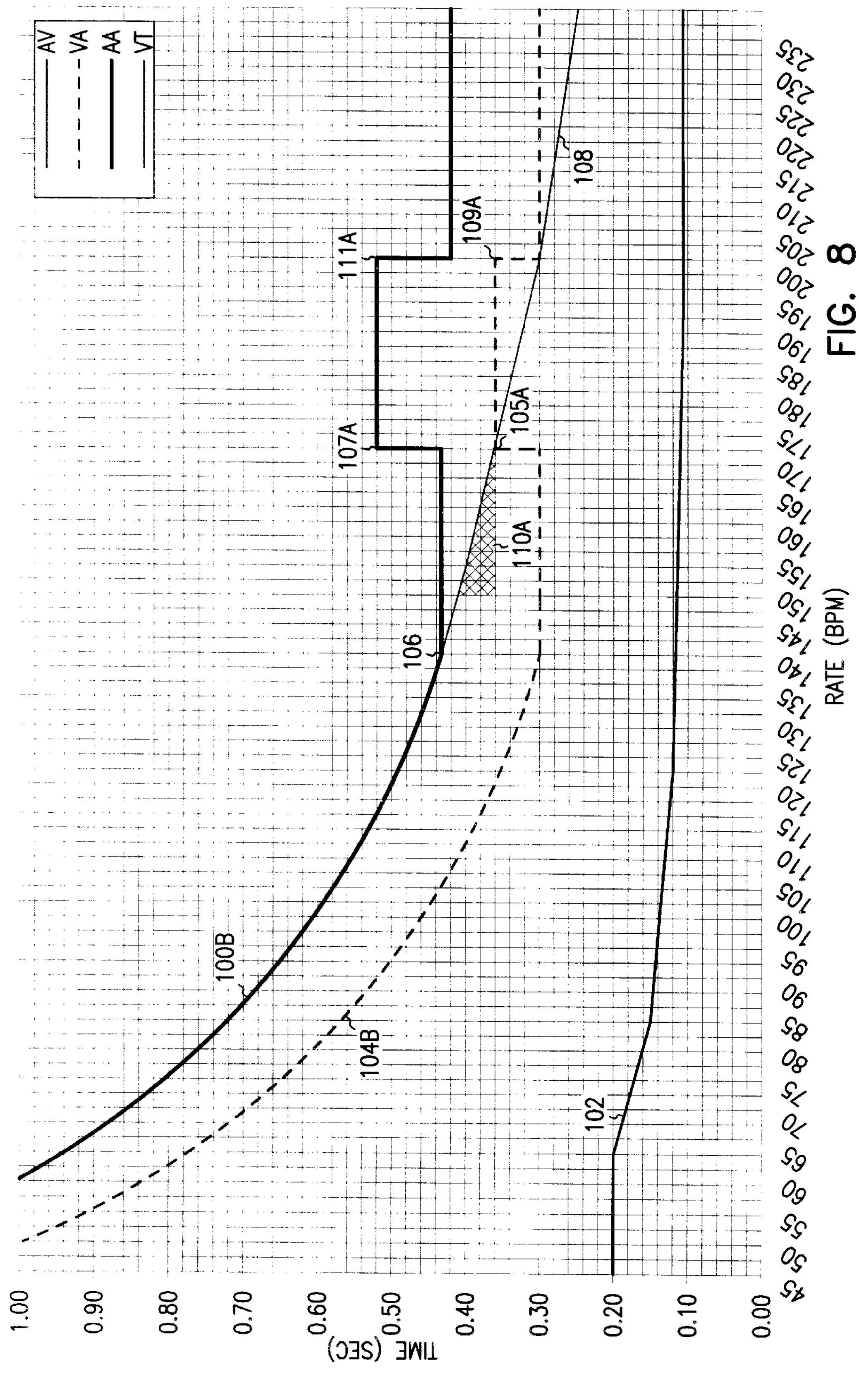
FIG. 8 illustrates a graphical representation of basic time intervals versus rate for an alternate embodiment of FIG. 7.

In the techniques described in reference to FIGS. 6–8, it should be noted that the VA interval curve 104A, 104B remains above the VT interval curve 108 throughout most of the region of interest. Because the lengthening of the VA interval lengthens the AA interval, and thus reduces the MAR, it may be desirable to use a technique which sets the VA interval curve 104 at or slightly above the VT interval curve 108 and allows the VA interval curve 104 to follow the VT interval curve 108. A technique of this type allows the MPR to increase steadily back to its normal level as the VT interval shortens.

Figure 9:
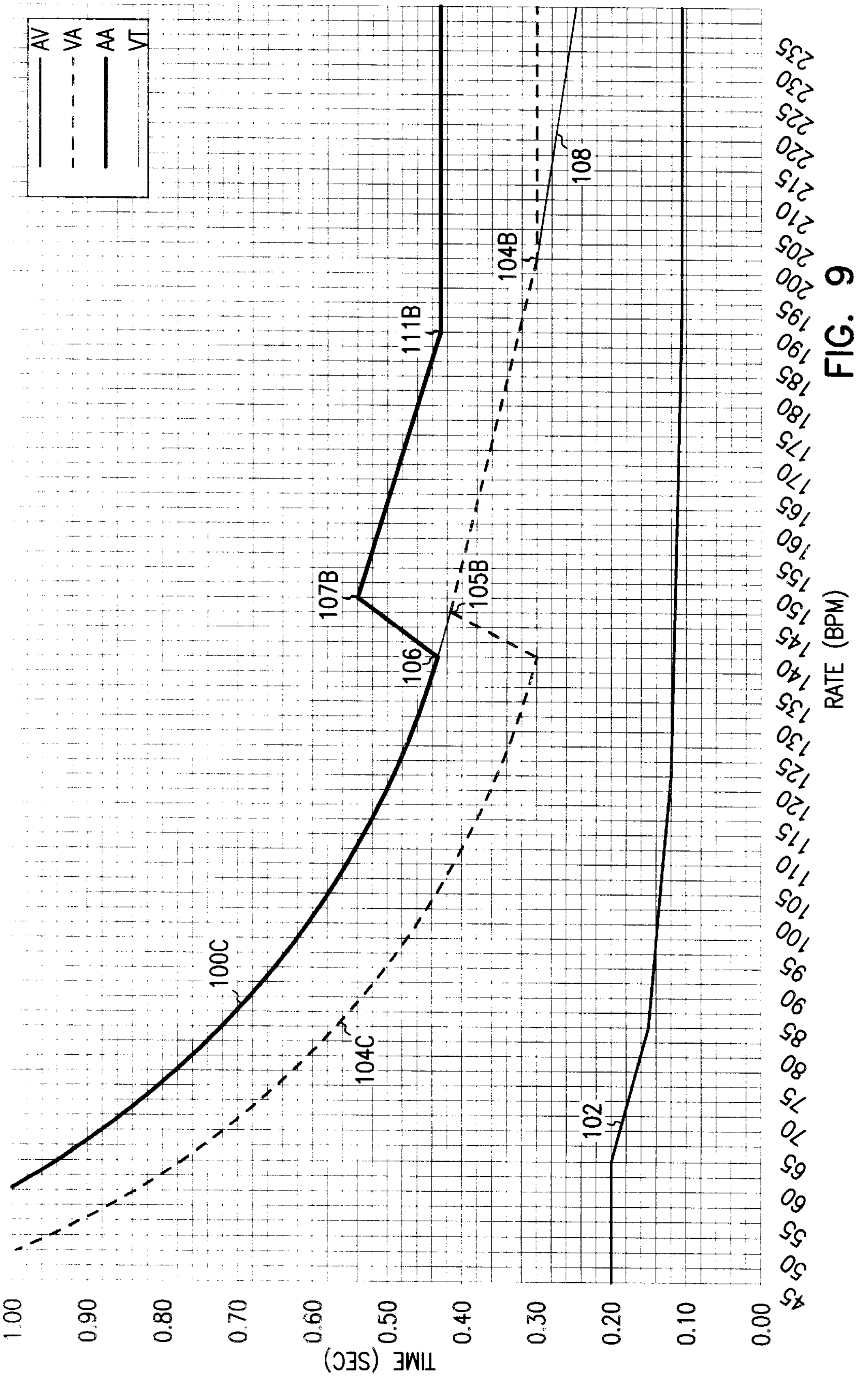
FIG. 9 illustrates a graphical representation of basic time intervals versus rate for an alternate embodiment of a dual-chamber cardiac stimulator in accordance with the present invention.
Figure 10:
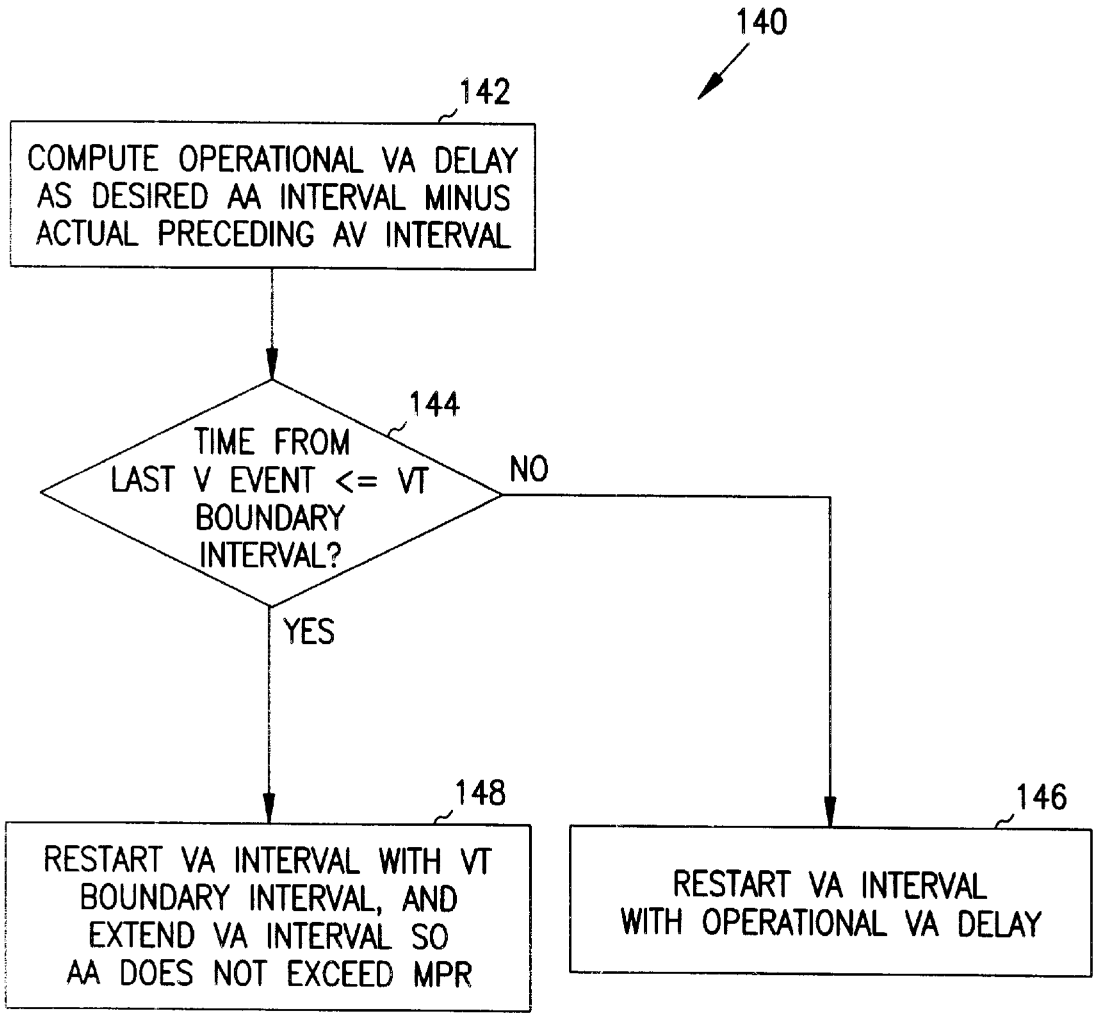
FIG. 10 illustrates a flow chart depicting the functioning of a cardiac stimulator in accordance with FIG. 9.

An example of this type of technique is illustrated in FIGS. 9 and 10. It should be noted that identical or similar reference numerals and the same MPR and tachycardia rate detection boundary are used in FIG. 9 as in the previous FIGS. 5 and 6. In particular, it should be noted that the AV interval curve 102 and the VT interval curve 108 are the same in this example as in the example illustrated in FIGS. 5 and 6. However, it should be noted that the VA interval curve 104C is skewed upwardly at about the VT rate detection boundary of 150 BPM, as illustrated by the point 105B. Indeed, as illustrated by the VA interval curve 104C in FIG. 9, the VA interval is lengthened at about the VT rate detection boundary to make it equal to or greater than the longest VT interval illustrated by the VT interval curve 108. Due to the additive effects of the AV interval curve 102 and the VA interval curve 104C, this action effectively increases the AA interval at point 107B, and thus reduces the atrial pacing rate, slightly in the presence of high rate ventricular activity. Thus, it should be noted that the AA interval curve 100C skews upwardly in a manner similar to that of the VA interval curve 104C. It should also be noted that this action removes the triangle 110. As the ventricular activity rises from about 150 BPM through about 190 BPM, the VA curve 104C and the AA curve 100C follow a similar downward slope until they drop back to previous levels at points 109B and 111B, respectively.

Referring additionally to FIG. 10, when any ventricular event is detected at or above the VT rate detection boundary, the VA interval is restarted with the larger of the VT boundary interval or the operational VA delay. The operational VA delay is defined as the desired AA interval minus the actual proceeding AV interval. In a specific example illustrated in the flow chart 140, when a ventricular event at or above the VT rate detection boundary is detected, the operational VA delay is computed (Block 142). It is then determined whether the time from the last ventricular event, i.e., the VV interval, is less than or equal to the VT boundary interval. (Block 144). If the VV interval is less than or equal to the VT rate detection boundary, the detected ventricular event is not a ventricular tachycardia Therefore, the cardiac stimulator continues to operate in the region of the graph to the left of the MPR 106. Accordingly, the VA interval is restarted with the operational VA delay as illustrated in both FIGS. 5 and 9. (Block 146).

However, if the VV interval is greater than the VT rate detection boundary, then the ventricular event is indicative of a ventricular tachyarrhythmia. Thus, the cardiac stimulator begins to operate in the region of the graph of FIG. 9 to the right of the MPR 106. Thus, the VA interval is restarted with the VT boundary interval and the VA interval is extended so that the AA interval does not exceed the MPR. (Block 148). As mentioned earlier, this action essentially moves the VA interval curve 104C upwardly to the VT boundary rate interval and causes it to follow the VT interval curve 108. This action has the effect of slowing the pacing rate, as evidence by the similarly displaced AA interval curve 100C, so that atrial pacing events are precluded until the ventricular tachycardia maybe sensed and treated. It should also be noted that another ventricular tachycardia rate boundary, such as the TACH-1/TACH-2 boundary, may be substituted for the VT boundary rate interval in this technique in much the same manner as described in FIG. 8.

Figure 11:
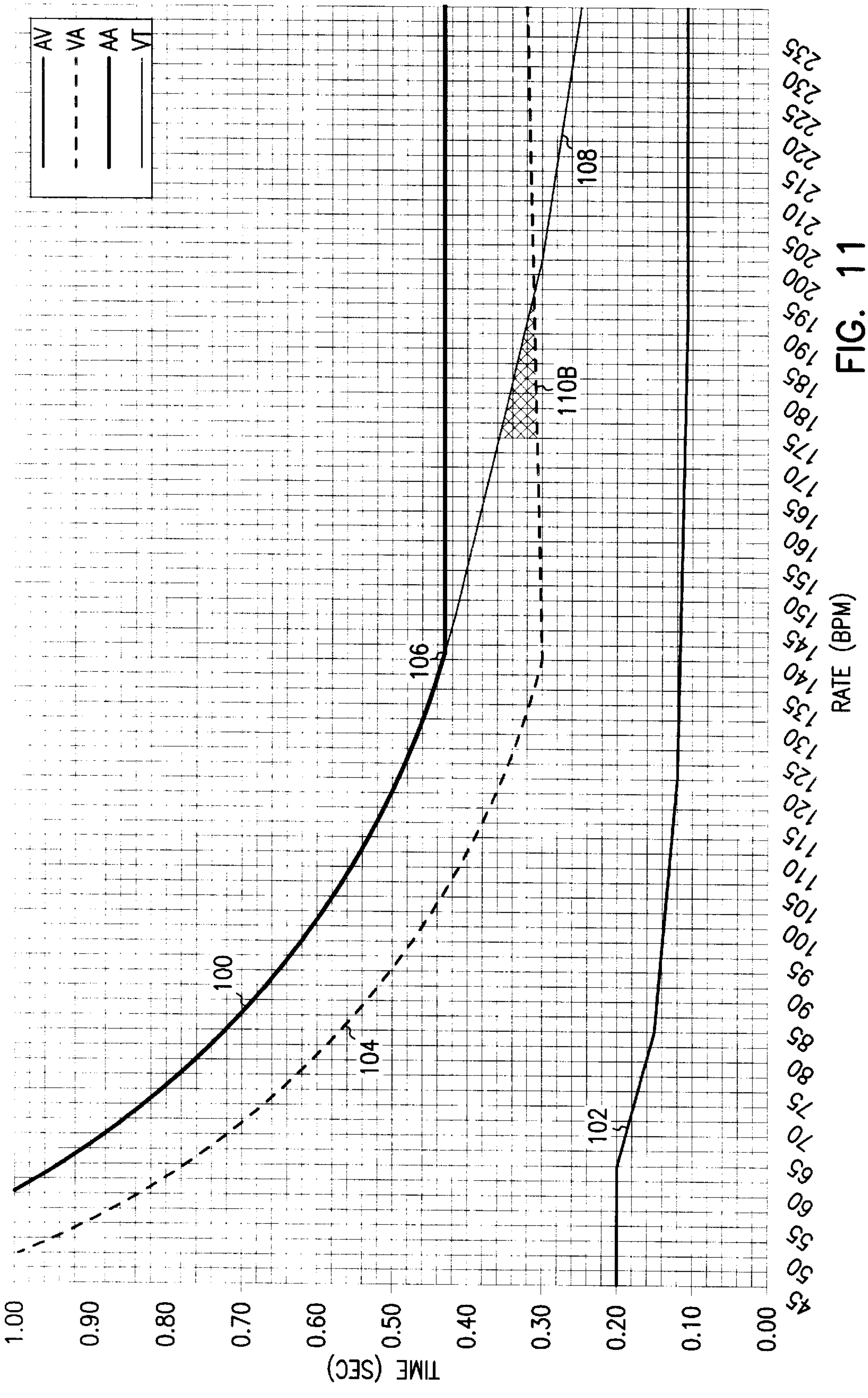
FIG. 11 illustrates a graphical representation of basic time intervals versus rate for an alternate embodiment of a dual-chamber cardiac stimulator in accordance with the present invention, where the VT boundary rate is set higher than the intersection of the VT and VA curves.

Although the techniques described above with reference to FIGS. 6–10 involve curve shifting which induces tachycardia hysteresis, various other actions may be taken alone, or in combination, to improve the ability of a cardiac stimulator to detect ventricular tachyarrhythmias which might otherwise be obscured by an atrial pacing event. As discussed previously, the cardiac stimulator 10 is advantageously programmable. Thus, the programmable ranges of various parameters may be restricted to reduce or eliminate the circumstance in which atrial pacing obscures ventricular tachyarrhythmias. For example, the VT rate detection boundary may be set higher than the intersection of the VT interval curve 108 and the VA interval curve 104. Thus, in this example, the VT rate detection boundary would be set at about 190 BPM. Although this action may be suitable for certain patients that can tolerate ventricular tachyarrhythmias in the range below 190 BPM, such action would typically not fit the needs of most patients. Of course, as illustrated in FIG. 11, the VT rate detection boundary may be set at an intermediate point such as the intersection between the TACH-1 range and the TACH-2, range in instances where a patient may tolerate a certain range of ventricular tachyarrhythmia rather well. OF course, it should be understood that such action only has the effect of decreasing the size of the region, illustrated by the triangle 110B, where ventricular tachyarrhythmia may be obscured by atrial pacing, but it does so at the expense of disabling the cardiac stimulator from detecting any ventricular tachyarrhythmias up to the TACH-2 boundary.

Figure 12:
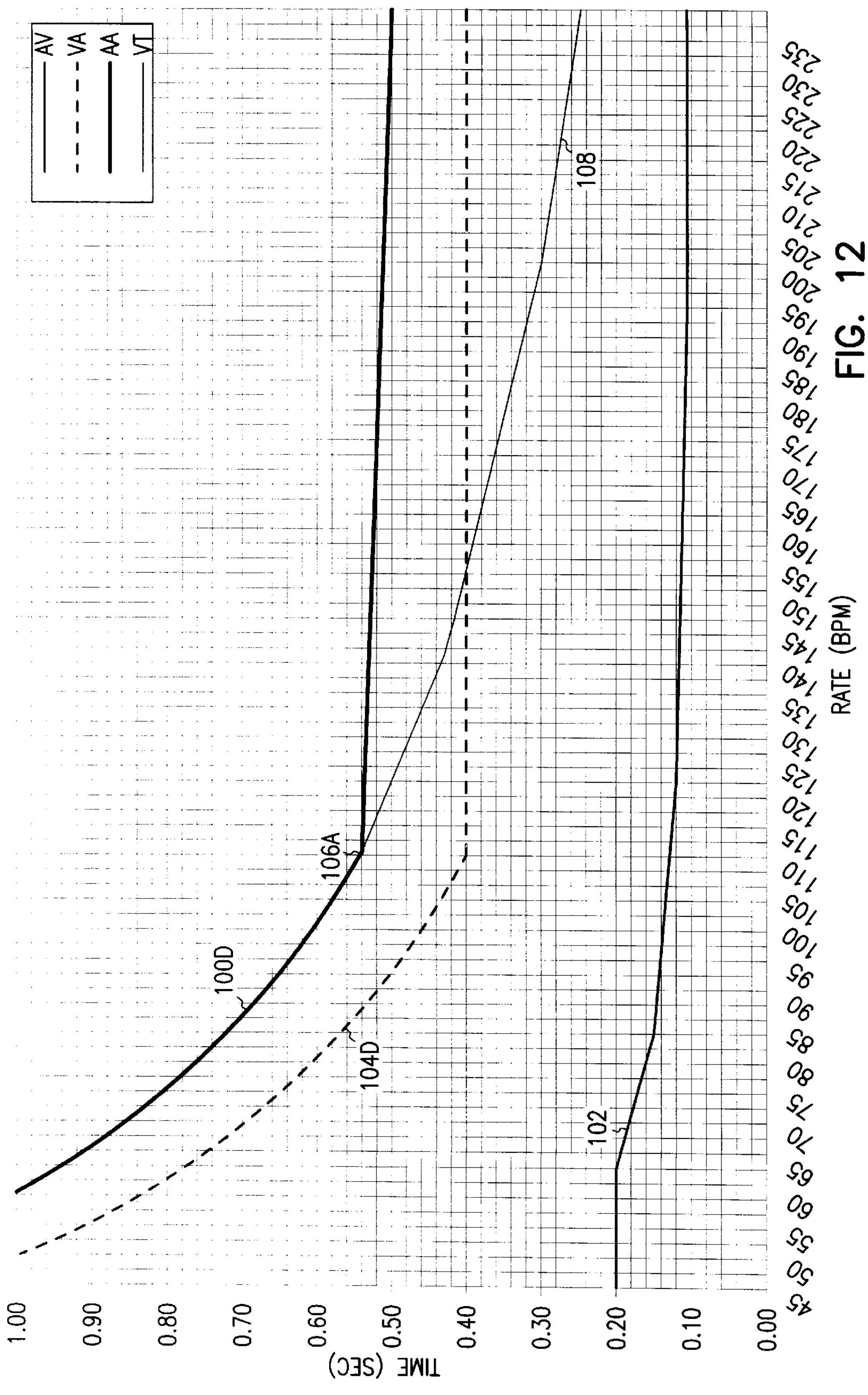
FIG. 12 illustrates a graphical representation of basic time intervals versus rate for an alternate embodiment of a dual-chamber cardiac stimulator, where the maximum pacing rate is set low enough so that the resulting VA curve is raised above the VT curve in the region above the VT boundary.

As illustrated in FIG. 12, the MPR may be set low enough so that the resulting VA interval curve 104D is raised above the VT interval curve 108 in the region above the VT rate detection boundary. However, it can be seen that this action may significantly limit the MPR 106. For instance, as illustrated in this example by the AA interval curve 100D, the MPR must be limited to approximately 110 BPM in order to raise the VA interval curve 104D above the VT interval curve 108 in the region above the VT rate detection boundary.

Figure 13:
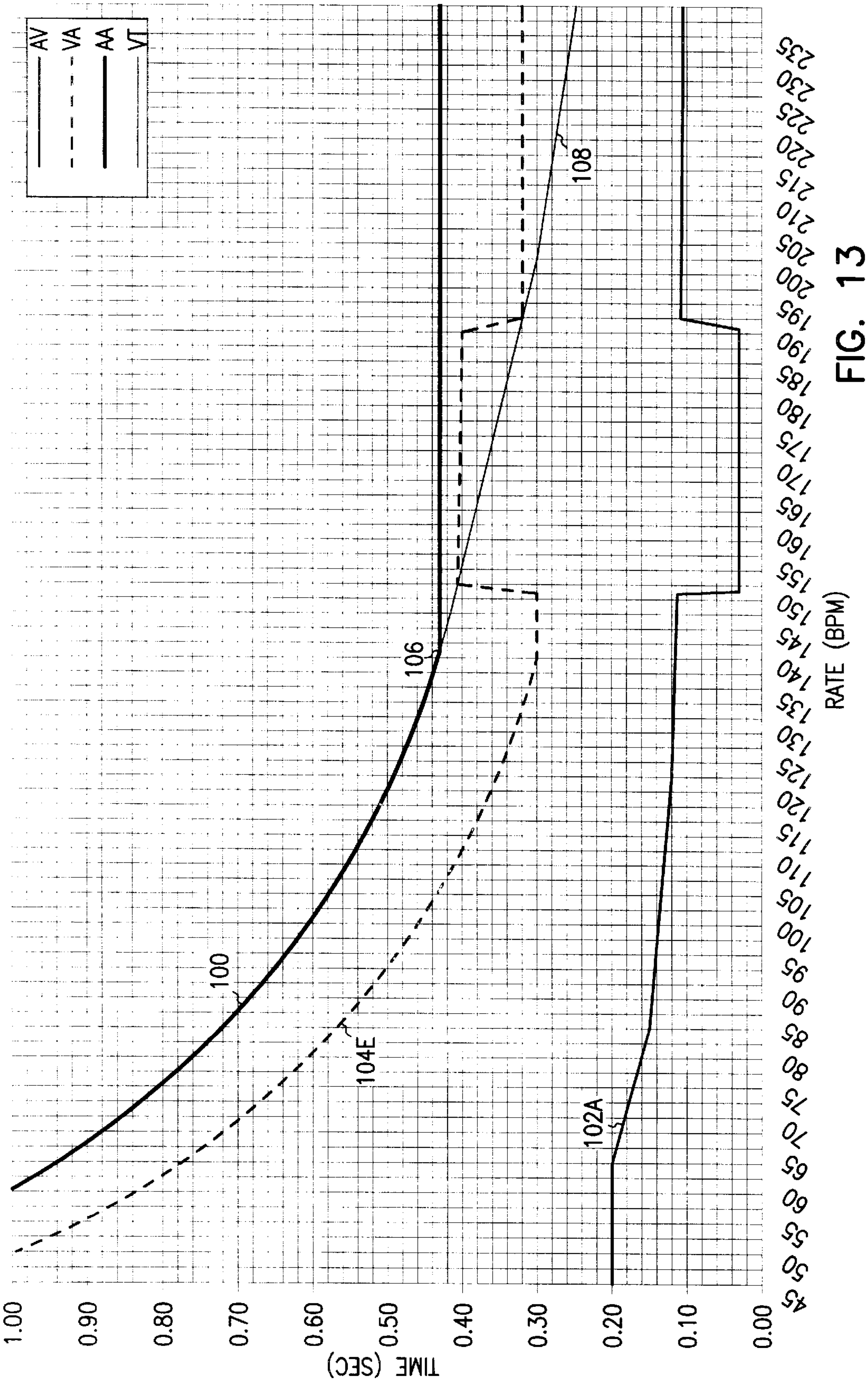
FIG. 13 illustrates a graphical representation of basic time intervals versus rate for an alternate embodiment of a dual-chamber cardiac stimulator in accordance with the present invention, where the interval is reduced so that the resulting VA curve is raised above the VT curve in the region above the VT boundary.

As another example, the AV interval curve 102A may be reduced so that the resulting VA interval curve 104E is raised above the VT interval curve 108 in the region above the VT rate detection boundary, as illustrated in FIG. 13. This action has the effect of retaining the desired VT rate detection boundary and the desired MPR However, the shortened AV interval may cause problems such as inadequate ventricular filling. Of course, the three techniques described in FIGS. 11, 12, and 13 may be used in selected combinations to program the cardiac stimulator 10 to best fit a particular patient's needs while minimizing the range in which ventricular tachyarrhythmias may be obscured by an atrial pacing event.

The techniques described above are advantageously embodied as software routines and/or programing limits that are resident in the memory 36 of the cardiac stimulator 10 and executed by the microprocessor 32. Such routines may be programmed into the cardiac stimulator 10 at the time of manufacturing, or they may be loaded afterward via the programmer 35. Of course, these techniques could also be implemented by an appropriate state machine or other suitable hardware, or by a combination of hardware and software.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A cardiac stimulator comprising:

a ventricular circuit adapted to deliver a ventricular signal indicative of a ventricular event;

an atrial circuit adapted to deliver an atrial signal indicative of an atrial event and adapted to deliver electrical stimulation to the atrium of the heart; and a control circuit executing an algorithm for controlling the cardiac stirnulator, the control circuit being coupled to the atrial circuit and to the ventricular circuit to receive the atrial and ventricular signals, the algorithm:

determining an interval between successive ventricular events, referred to as a VV interval, determining an operational VA delay by subtracting an AV interval from an AA interval, determining whether the VV interval is less than a ventricular tachyarrhythmia boundary interval, if the VV interval is less than the boundary interval, restarting a VA interval with the operational VA delay, if the VV interval is not less than the boundary interval, determining whether the operational VA delay is less than the boundary interval, restarting the VA interval with the operational VA delay in response to the operational VA delay not being less than the boundary interval, and restarting the VA interval with the boundary interval in response to the operational VA delay being less than the boundary interval.

2. The cardiac stimulator, as set forth in claim 1, wherein the boundary interval defines an interval between normal sinus rate and a ventricular tachyarrhythmia.

3. The cardiac stimulator, as set forth in claim 1, wherein the boundary interval defines an interval between a well-tolerated ventricular tachyarrhythmia and a moderately-tolerated ventricular tachyarrhythmia.

4. A method of operating a cardiac stimulator comprising the acts of:

determining an operational VA delay by subtracting an AV interval from an AA interval, deterring whether a VV interval is less than a ventricular tachyarrhythmia boundary interval, if the VV interval is not less than the boundary interval, restarting a VA interval with the operational VA delay, if the VV interval is less than the boundary interval, determining whether the operational VA delay is less than the boundary interval, restarting the VA interval with the operational VA delay in response to the operational VA delay not being less than the boundary rate interval, and restarting the VA interval with the boundary interval in response to the operational VA delay being less than the boundary interval.

5. The method, as set forth in claim 4, wherein the boundary interval defines an interval between normal sinus rate and a ventricular tachyarrhythmia.

6. The method, as set forth in claim 4, wherein the boundary interval defines an interval between a well-tolerated ventricular tachyarrhythmia and a moderately-tolerated ventricular tachyarrhythmia.

7. A method of operating a cardiac stimulator comprising the acts of:

determining an operational VA delay by subtracting an AV interval from an AA interval, determining whether a W interval is less than a ventricular tachyarrhythmia boundary interval, if the VV interval is not less than the boundary interval, restarting a VA interval with the operational VA delay, and if the VV interval is less than the boundary interval, restarting the VA interval with the boundary interval.

8. The method, as set forth in claim 7, wherein the boundary interval defines an interval between normal sinus rate and a ventricular tachyarrhythmia.

9. The method, as set forth in claim 7, wherein the boundary interval defines an interval between a well-tolerated ventricular tachyarrhythmia and a moderately-tolerated ventricular tachyarrhythmia.

10. A cardiac stimulator comprising:

a control circuit including: computational circuitry adapted to determine an operational VA delay by subtracting an AV interval from an AA interval; detection circuitry adapted to determine whether a ventricular tachyarrhythmia is present; and timing circuitry adapted to time a VA interval determined based on whether the ventricular tachyarrhythmia is present and at least one of the operational VA delay and a predetermined ventricular tachyarrhythmia rate boundary interval; and an atrial stimulus generator adapted to deliver a pace at the end of the VA interval.

11. The cardiac stimulator, as set forth in claim 10, wherein the timing circuitry includes a timer with restart circuitry, and wherein the VA interval is set to the ventricular tachyarrhythmia rate boundary interval if the ventricular tachyarrhythmia is present and the operational VA delay is less than the ventricular tachyarrhythmia rate boundary interval.

12. The cardiac stimulator, as set forth in claim 11, wherein the VA interval is set to the operational VA delay if the ventricular tachyarrhythmia is present and the operational VA delay is not less than the ventricular tachyarrhythmia rate boundary interval.

13. The cardiac stimulator, as set forth in claim 12, wherein the VA interval is set to the operational VA delay if the ventricular tachyarrhythmia is not present.

14. The cardiac stimulator, as set forth in claim 13, wherein the detection circuitry includes a comparator having a first input representative of a VV interval, a second input representative of the ventricular tachyarrhythmia rate boundary interval, and an output representative of whether the ventricular tachyarrhythmia is present.

15. The cardiac stimulator, as set forth in claim 10, wherein the timing circuitry includes a timer with restart circuitry, and wherein the VA interval is set to the ventricular tachyarrhythmia rate boundary interval, if the ventricular tachyarrhythmia is present.

16. The cardiac stimulator, as set forth in claim 15, wherein the VA interval is set to the operational VA delay if the ventricular tachyarrhythmia is not present.

17. The cardiac stimulator, as set forth in claim 16, wherein the detection circuitry includes a comparator having a first input representative of a VV interval, a second input representative of the ventricular tachyarrhythmia rate boundary interval, and an output representative of whether the ventricular tachyarrhythmia is present.

18. A method of operating a cardiac stimulator, the method comprising:

determining an operational VA delay by subtracting an AV interval from an AA interval;

detecting a ventricular tachyarrhythmia;

determining a VA interval based on whether the ventricular tachyarrhythmia is present and at least one of the operational VA delay and a predetermined ventricular tachyarrhythmia rate boundary interval; and delivering a pace at the end of the VA interval.

19. The method, as set forth in claim 18, wherein determining the VA interval includes setting the VA interval to the ventricular tachyarrhythmia rate boundary interval if the ventricular tachyarrhythmia is detected and the operational VA delay is less than the ventricular tachyarrhythmia rate boundary interval.

20. The method, as set forth in claim 19, wherein determining the VA interval further includes setting the VA interval to the operational VA delay if the ventricular tachyarrhythmia is detected and the operational VA delay is not less than the ventricular tachyarrhythmia rate boundary interval.

21. The method, as set forth in claim 20, wherein determining the VA interval further includes setting the VA interval to the operational VA delay if the ventricular tachyarrhythmia is not detected.

22. The method, as set forth in claim 21, wherein the predetermined ventricular tachyarrhythmia rate boundary interval is a predetermined VV interval corresponding to one of:

a first boundary between a normal sinus rate and a ventricular tachyarrhythmia rate; and a second boundary between a well-tolerated ventricular tachyarrhythmia rate and a moderately-tolerated ventricular tachyarrhythmia rate.

23. The method, as set forth in claim 22, wherein detecting the ventricular tachyarrhythmia includes:

comparing a VV interval to the ventricular tachyarrhythmia rate boundary interval; and declaring a ventricular tachyarrhythmia if the VV interval is less than the ventricular tachyarrhythmia rate boundary interval.

24. The method, as set forth in claim 18, wherein determining the VA interval includes setting the VA interval to the ventricular tachyarrhythmia rate boundary interval if the ventricular tachyarrhythmia is detected.

25. The method, as set forth in claim 24, wherein determining the VA interval includes setting the VA interval to the operational VA delay if the ventricular tachyarrhythmia is not detected.

26. The method, as set forth in claim 25, wherein the predetermined ventricular tachyarrhythmia rate boundary interval is a predetermined VV interval corresponding to one of:

a first boundary between a normal sinus rate and a ventricular tachyarrhythmia rate; and a second boundary between a well-tolerated ventricular tachyarrhythmia rate and a moderately-tolerated ventricular tachyarrhythmia rate.

27. The method, as set forth in claim 26, wherein detecting the ventricular tachyarrhythmia includes:

comparing a VV interval to the ventricular tachyarrhythmia rate boundary interval; and declaring a ventricular tachyarrhythmia if the VV interval is less than the ventricular tachyarrhythmia rate boundary interval.

* * * * *

UNITED STATES PATENT AND TRADEMARK OFFICE
CERTIFICATE OF CORRECTION

PATENT NO. : 6,510,343 B2
DATED : January 21, 2003
INVENTOR(S) : Randolph K. Armstrong and Douglas J. Cook It is certified that error appears in the above-identified patent and that said Letters Patent is hereby corrected as shown below:

Title page,
Item [56], References Cited, U.S. PATENT DOCUMENTS, delete "9/1985" and insert -- 6/1985 -- therefor.
Item [57], ABSTRACT,
Line 4, insert -- . -- after "tachyarrhythmia".

Column 16,
Line 54, delete "W" and insert -- V V -- therefor.

Signed and Sealed this

Third Day of February, 2004

JON W. DUDAS
*Acting Director of the United States Patent and Trademark Office*